United States Patent
Ewald et al.

(10) Patent No.: US 11,669,636 B2
(45) Date of Patent: Jun. 6, 2023

(54) MEDICAL DATA COLLECTION FOR MACHINE LEARNING

(71) Applicant: KONINKLIJKE PHILIPS N.V., Eindhoven (NL)

(72) Inventors: Arne Ewald, Hamburg (DE); Tim Nielsen, Hamburg (DE); Karsten Sommer, Hamburg (DE); Irina Waechter-Stehle, Hamburg (DE); Christophe Michael Jean Schülke, Hamburg (DE); Frank Michael Weber, Hamburg (DE); Rolf Jürgen Weese, Hamburg (DE); Jochen Peters, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 393 days.

(21) Appl. No.: 16/814,249

(22) Filed: Mar. 10, 2020

(65) Prior Publication Data
US 2020/0293690 A1  Sep. 17, 2020

(30) Foreign Application Priority Data
Mar. 11, 2019 (EP) .................................... 19161895

(51) Int. Cl.
*G06F 21/62* (2013.01)
*G16H 10/60* (2018.01)
(Continued)

(52) U.S. Cl.
CPC ......... *G06F 21/6254* (2013.01); *G06N 20/00* (2019.01); *G16H 10/60* (2018.01); *G16H 30/20* (2018.01)

(58) Field of Classification Search
CPC .... G06F 21/6254; G16H 10/60; G16H 30/20; G06N 20/00
See application file for complete search history.

(56) References Cited

U.S. PATENT DOCUMENTS

| 2013/0054467 A1* | 2/2013 | Dala .................. G06F 21/6245 705/51 |
| 2013/0167192 A1* | 6/2013 | Hickman ............ G06F 21/6245 726/1 |

(Continued)

FOREIGN PATENT DOCUMENTS

WO   2018174873 A1   9/2018

OTHER PUBLICATIONS

"CometCloudCare (C3): Distributed Machine Learning Platform-as-a-Service with Privacy Preservation" by Potluru, Vamsi K. et al, Neural Information Processing Systems (NIPS), Dec. 8-13, 2014.

(Continued)

*Primary Examiner* — Darshan I Dhruv (57) ABSTRACT

A system (100) and computer-implemented method are provided for data collection for distributed machine learning of a machine learnable model. A privacy policy data (050) is provided defining computer-readable criteria for limiting a selection of medical image data (030) to a subset of the medical image data to obfuscate an identity of the at least one patient. The medical image data is selected based on the computer-readable criteria to obtain privacy policy-compliant training data (060) for transmission to another entity. The system and method enable medical data collection at clinical sites without requiring manual oversight, and enables such selections to be made automatically, e.g., based on a request for medical image data which may be received from outside of the clinical site.

9 Claims, 4 Drawing Sheets

(51) Int. Cl.
    *G16H 30/20*        (2018.01)
    *G06N 20/00*        (2019.01)

(56) References Cited

U.S. PATENT DOCUMENTS

| | | | |
|---|---|---|---|
| 2016/0283738 A1* | 9/2016 | Wang | G06N 20/00 |
| 2017/0372096 A1* | 12/2017 | Yousfi | G16H 10/60 |
| 2018/0018590 A1* | 1/2018 | Szeto | G06N 20/10 |
| 2018/0129900 A1* | 5/2018 | Kiraly | G06N 3/08 |
| 2019/0057763 A1* | 2/2019 | Stockert | G16H 10/00 |
| 2019/0156061 A1* | 5/2019 | Chakraborty | H04L 63/0421 |
| 2020/0082290 A1* | 3/2020 | Pascale | G06F 21/6254 |
| 2020/0211692 A1* | 7/2020 | Kalafut | G06N 20/00 |
| 2020/0285771 A1* | 9/2020 | Dey | G06F 21/6272 |
| 2021/0150358 A1* | 5/2021 | Lansel | G06F 16/9014 |

OTHER PUBLICATIONS

Tom Brosch; Axel Saalbach; Foveal fully convolutional nets for multi-organ segmentation; Proceedings vol. 10574, Medical Imaging 2018: Image Processing; 105740U (2018).

Brosch, T. et al., "Foveal fully convolutional nets for multi-organ segmentation", 2018, vol. 10574.

Itay Lieder, Yehezkel Resheff, Tom Hope, "Learning TensorFlow a Guide to Building Deep Learning Systems", O'Reilly Media 2017.

* cited by examiner

MEDICAL DATA COLLECTION FOR MACHINE LEARNING

CROSS-REFERENCE TO PRIOR APPLICATIONS

This application claims the benefit of European Patent Application No. 19161895.8, filed on 11 Mar. 2019. This application is hereby incorporated by reference herein.

FIELD OF THE INVENTION

The invention relates to a system and computer-implemented method for collecting medical data for machine learning of a machine learnable model. The invention further relates to a system and computer-implemented method for training the machine learnable model using training data obtained from at least one other system. The invention further relates to a computer-readable medium comprising instructions to perform one of the computer-implemented methods.

BACKGROUND OF THE INVENTION

The success of machine learning algorithms for medical image analysis relies to a large extent on the availability of a large amount of medical image data together with corresponding labels, also referred to as annotations.

While medical image data and labels may be available in clinical settings, e.g., at clinical sites such as hospitals, increasingly strict privacy regulations make it difficult to transfer such medical image data outside of the clinical setting, e.g., to a development site, in order to perform machine learning there. Namely, such transfer of medical image data typically relies on approvals, such as patient consent, consent of Institutional Review Board (IRB) and compliance to company internal privacy procedures. Obtaining such approvals is typically a lengthy process.

The publication "*CometCloudCare (C3): Distributed Machine Learning Platform-as-a-Service with Privacy Preservation*" by Potluru, Vamsi K. et al, Neural Information Processing Systems (NIPS), 8-13 Dec. 2014, describes a platform, termed CometCloudCare (C3), which is said to enable the use and development of distributed machine learning algorithms that can take advantage of geographically distributed resources. Users are envisioned with two roles: regular users and power users. Regular users may simply select a desired machine learning algorithm and privacy policy from a catalogue and specify what datasets they want to use, while power users can create new machine learning algorithms and privacy policies. The privacy policies are provided as an integral part of the distributed machine learning algorithms, namely as a differentially private distributed algorithm part.

Disadvantageously, it may be complex to incorporate privacy policies into the machine learning algorithm itself. Additionally, it may not always be desired to perform the machine learning itself in a distributed manner.

SUMMARY OF THE INVENTION

It may be desirable to obtain a system or computer-implemented method to collect medical data for machine learning of a machine learnable model by which the identity of patients associated with the collected medical data is obfuscated. Such a system or method may be used for data collection at clinical sites, such as hospitals, to obtain privacy-compliant training data for the machine learning, which may then be performed elsewhere, e.g., at a development site.

In accordance with a first aspect of the invention, a system is provided for data collection for machine learning of a machine learnable model.

The system comprises:
an input interface for accessing:
  medical image data of at least one patient and label data defining labels associated with the medical image data;
  privacy policy data defining one or more computer-readable criteria for limiting a selection of the medical image data to a subset of the medical image data to obfuscate an identity of the at least one patient;
a communication interface to another entity associated with the machine learning of the machine learnable model;
a processor subsystem configured to:
  based on the one or more computer-readable criteria, perform the selection of the medical image data and an associated selection of the label data to obtain privacy policy-compliant training data;
  via the communication interface, transmit the privacy policy-compliant training data to the other entity to enable the machine learnable model to be trained on the basis of the privacy policy-compliant training data.

In accordance with a further aspect of the invention, a computer-implemented method is provided for data collection for distributed machine learning of a machine learnable model. The method comprises:
accessing:
  medical image data of at least one patient and label data defining labels associated with the medical image data;
  privacy policy data defining one or more computer-readable criteria for limiting a selection of the medical image data to a subset of the medical image data to obfuscate an identity of the at least one patient;
based on the one or more computer-readable criteria, performing the selection of the medical image data and an associated selection of the label data to obtain privacy policy-compliant training data;
via a communication interface, transmitting the privacy policy-compliant training data to another entity to enable the machine learnable model to be trained on the basis of the privacy policy-compliant training data.

The above measures involve a system and method accessing medical image data of at least one patient and associated labels. For example, the medical image data may represent one or more 2D images, 3D volumetric images, time-series of 2D images, etc, or any combination of such types of medical image data. The labels may have been manually generated or obtained in an automatic manner, and may directly relate to the image content, e.g., by identifying lesions in the medical image data, by providing a segmentation of an anatomical structure in the medical image data, etc. In other examples, the labels may represent metadata which indirectly relates to the image content, e.g., by representing parameters of an image acquisition apparatus which is used for the image acquisition.

In addition, privacy policy data is accessed which defines one or more computer-readable criteria for limiting a selection of the medical image data to a subset of the medical image data. More specifically, the computer-readable criteria limit the selection of the medical image data to a subset of the medical image data by which the identity of the patient(s) to which the medical image data pertains is obfuscated. Here, the term 'obfuscated' refers to the associability of the medical image data to the particular patient(s) being eliminated or at least reduced, e.g., made more difficult. For example, if the medical image data is volumetric image data, the privacy policy data may limit the selection of volumetric image data to one or more sub-volumes of the volumetric image which are each, in terms of volume, below a first threshold and have a combined volume below a second threshold.

A selection is then performed of the medical image data which is in compliance with the privacy policy made operational by the computer-readable criteria. A corresponding selection is obtained of the labels associated with the medical image data, either as a separate step or as an integral part of the earlier selection. As a result, privacy policy-compliant training data is obtained which is then transmitted via a communication interface to another entity which may perform the training of a machine learnable model on the basis of the privacy policy-compliant training data, or at least process the training data as a precursor to said training. The above-described system is therefore also referred to 'data collection system'. The other entity may, more specifically, be an external entity, such as the training system performing the training, or another part of the data collection system, e.g., an evaluation subsystem, as also described elsewhere in this specification.

The selection of medical image data is thereby limited in such a way that the identity of the patient(s) associated with the medical image data is obfuscated. Thereby, privacy control is established for the collection of medical image data, in that only medical image data is allowed to be selected and subsequently transmitted which adheres to the privacy policy made operational by the one or more computer-readable criteria. The above measures thereby enable medical data collection at clinical sites without requiring manual oversight, and enables such selections to be made automatically, e.g., based on a request for medical image data which may be received from outside of the clinical site.

In accordance with a further aspect of the invention, a system is provided for training a machine learnable model using training data obtained from at least one other system, such as the above-described data collection system.

The system comprises:
a network interface to a network;
a processor subsystem configured to:
via the network interface, request the at least one other system to transmit training data associated with a selection of medical image data;
via the network interface and in response to said request, receive the training data from the at least one other system; and
train the machine learnable model based on the training data.

In accordance with a further aspect of the invention, a computer-implemented method is provided for training a machine learnable model using training data obtained from a number of entities which are reachable via a network.

The method comprises:
via a network, requesting at least one of the entities to transmit training data associated with a selection of medical image data;
via the network and in response to said request, receiving the training data from the at least one entity; and
training the machine learnable model based on the training data.

The above measures involve a system and method requesting at least one entity to transmit training data associated with a selection of medical image data, and to perform the training of the machine learnable model based on the training data which is received from the at least one entity. The abovementioned system is therefore also referred to as 'training system'. These requests may be sent to several entities, and the training may be performed based on the training data obtained from these entities. Each entity may embody the aforementioned data collection system or computer-implemented method, and accordingly, receive the request for training data, identify which selection of the medical image data conforms to the request and the one or more computer-readable criteria, and then respond to the request by transmitting the privacy policy-compliant training data. Additionally or alternatively, if the request specifies the selection of the medical image data, each entity may identify whether the specified selection of the medical image data conforms to the one or more computer-readable criteria. If this is the case, the entity may respond by transmitting the specified selection as privacy policy-compliant training data, and if not, respond by refusing the request. Accordingly, requests for medical image data may be automatically verified against the privacy policy made operational by the computer-readable criteria, and if the request adheres to the privacy policy, may be automatically fulfilled, or only with limited human interaction.

Optionally, the one or more computer-readable criteria limit the selection of the medical image data to one or more image regions of the image volume. Each image region may represent a subset of the medical image data. Additionally or alternative, if several image regions may be selected, the several image regions together may represent a subset of the medical image data. Such image regions may take various forms depending on the type of medical image data, and may generally represent spatial image regions, or if the medical image data has a time-component, spatiotemporal image regions. For example, for 2D images, an image region may correspond to a 2D image region, also referred to as an image patch. For volumetric (3D) images, an image region may correspond to a sub-volume. For a time-series of 2D images (also referred to as 2D+T), an image region may correspond to a spatiotemporal (2D+T) region across the time-series of 2D images. Limiting the selection to an image region has been found to be an efficient mechanism of limiting the selection of the medical image data to a subset of the medical image data which obfuscates an identity of the at least one patient.

For example, in accordance with a further optional aspect of the invention, the one or more computer-readable criteria may limit at least one of the group of: a number, an individual or aggregate size, and a distribution, of the one or more image regions per image or per patient. Such types of computer-readable criteria may be numerically defined, e.g., as a value, while the adherence may be simply determined by quantifying the selection and comparing said quantified selection against the numerical value. For example, the computer-readable criteria may limit the selection to 5 sub-volumes each having size below 5% of the overall image volume. Such criteria may be defined per image, per patient or both. The distribution may be a spatial, temporal and/or spatiotemporal distribution. Distribution-based criteria may for example be used to establish a minimum spatial and/or temporal distance between selected image regions, e.g., to prevent selection of spatially and/or temporally adjacent image regions. Distribution-based criteria may also be used to establish a spatial and/or temporal randomness in the selection.

Optionally, the processor subsystem of the data collection system is configured to apply a machine learning data augmentation technique to the medical image data before selecting and transmitting the privacy policy-compliant training data to the other entity. While the privacy policy may limit the available training data, such data augmentation techniques may again be used to increase the available training data. Examples of data augmentation include, but are not limited to, deformation of image volumes and modification of grey-values of the image data. Data augmentation may further contribute to the obfuscation of the identity of the patient, as such techniques may modify the original image data, thereby making it more difficult for such modified image data to be attributed to the original patient.

Optionally, the processor subsystem of the data collection system is configured to, before or when generating the privacy policy-compliant training data, obfuscating whether different subsets of the medical data, or different parts of a subset, belong to a same patient, and/or whether the subset of the medical image data, or a part of the subset, is augmented by a machine learning data augmentation technique. The medical image data may originally be attributable to respective patients, e.g., based on image metadata. While such metadata may be removed or processed to obfuscate the identity of the patient, it may also be purposefully obfuscated whether different subsets or parts of a subset belong to one and the same (unidentified) patient. This may further hinder identification of the patient. Likewise, it may be obfuscated whether the subset of the medical image data, or a part of the subset, is augmented by a machine learning data augmentation technique, or whether said subset/subset part represents non-augmented 'original' image data. This may again further hinder identification of the patient.

For example, in accordance with a further optional aspect of the invention, the processor subsystem may be configured for randomizing or pseudo-randomizing an identifier of each of the different subsets of the medical image data, and/or an identifier of each of the different parts of the subset.

Optionally, the data collection system is distributed over at least a privacy subsystem and a data collection subsystem, and the privacy subsystem is configured to receive the request and to generate instructions for the data collection subsystem to collect and subsequently transmit the selection of the medical image data which conforms to the request and the one or more computer-readable criteria to the other entity. Such partitioning may be used to distribute the functionality of the data collection systems over different physical entities, such as workstations, servers or the like, and/or over different virtualized entities, such as software processes.

Optionally, the communication interface is a network interface to a network, and the processor subsystem is configured to transmit the privacy policy-compliant training data via the network interface to a system configured for training the machine learnable model based on the privacy policy-compliant training data.

Optionally, the data collection system further comprises:
a further processor subsystem representing the other entity receiving the privacy policy-compliant training data via the communication interface;
a network interface to a network;
wherein the further processor subsystem is configured to:
via the network interface, receive a processing algorithm for processing the selection of the medical image data;
execute the processing algorithm to obtain a processing result;
via the network interface, transmit the processing result as training data to a training system which is configured to train the machine learnable model based on the processing result provided by the training data.

Optionally, the processor subsystem of the training system is configured to, via the network interface:
send a processing algorithm to the at least one other system for processing the selection of the medical image data;
receive as the training data a processing result resulting from an execution of the processing algorithm; and
train the machine learnable model based on the processing result.

Instead or in addition to transmitting the privacy policy-compliant training data to the training system, the training data may also be transmitted to a further processor subsystem of the data collection system, which may process the selection of the medical image data using a processing algorithm which may be received externally, e.g., via a network interface, and in some embodiments may be received from the training system itself. The further processor subsystem may effectively perform a pre-processing of the selected medical image data to obtain a processing result and transmit the processing result to the training system. This may further contribute to the obfuscation of the identity of patient(s). Namely, the processed result is typically less likely to attributable to respective patients than the original medical image data. For example, the pre-processing may be a first stage of the overall machine learning of the machine learnable model. In a specific example, if the machine learnable model is a deep neural network, the first layer(s) may be evaluated by the further processor subsystem and the resulting activations may be transmitted to the training system which may then evaluate the remaining layers based on the transmitted activations. In some embodiments, the training system may provide the processing algorithm to the data collection system, and thereby prescribe to the data collection system which type of processing is to be performed.

In accordance with a further aspect of the invention, a computer-readable medium is provided comprising transitory or non-transitory data representing instructions arranged to cause a processor system to perform either or both computer-implemented methods.

In accordance with a further aspect of the invention, a computer-readable medium is provided comprising transitory or non-transitory data representing privacy policy data defining one or more computer-readable criteria for limiting a selection of medical image data of at least one patient to a subset of the medical image data to obfuscate an identity of the at least one patient.

It will be appreciated by those skilled in the art that two or more of the above-mentioned embodiments, implementations, and/or optional aspects of the invention may be combined in any way deemed useful.

Modifications and variations of any computer-implemented method and/or any computer program product, which correspond to the described modifications and variations of a corresponding system, can be carried out by a person skilled in the art on the basis of the present description.

A person skilled in the art will appreciate that the system and method may be applied to multi-dimensional image data, e.g. to two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF REFERENCE NUMBERS

The following list of reference numbers is provided for facilitating the interpretation of the drawings and shall not be construed as limiting the claims.

| | |
|---|---|
| 020, 022 | data storage |
| 030 | medical image data |
| 040 | label data |
| 050 | privacy policy data |
| 060 | privacy policy-compliant training data |
| 070 | aggregated privacy policy-compliant training data |
| 080 | machine learnable model data |
| 100 | system for medical data collection |
| 120 | input interface |
| 122, 124 | data communication |
| 140 | processor subsystem |
| 160 | communication interface |
| 200 | system for training a machine learnable model |
| 220 | network interface |
| 240 | processor subsystem |
| 260 | input interface |
| 262, 264 | data communication |
| 300 | volumetric medical image |
| 310-314 | sub-volume |
| 400 | time-series of images slices |
| 410 | image region |
| 500, 502 | system for medical data collection |
| 510, 512 | data collection subsystem |
| 520 | internal data communication |
| 530, 532 | privacy policy subsystem |
| 540 | privacy policy-compliant training data |
| 550, 552 | evaluation subsystem |
| 560 | evaluation result |
| 570 | system for training a machine learnable model |
| 580 | request data |
| 590 | evaluation algorithm data |
| 600 | method for medical data collection |
| 610 | accessing labelled image data, privacy policy data |
| 620 | performing privacy policy-compliant selection |
| 630 | transmitting privacy policy-compliant training data |
| 700 | method for training a machine learnable model |
| 710 | requesting entity to transmit training data |
| 720 | receiving training data from entity |
| 725 | repeating steps for another entity |
| 730 | training model based on received training data |
| 800 | computer-readable medium |
| 810 | non-transitory data |

DETAILED DESCRIPTION OF EMBODIMENTS

Figure 1:
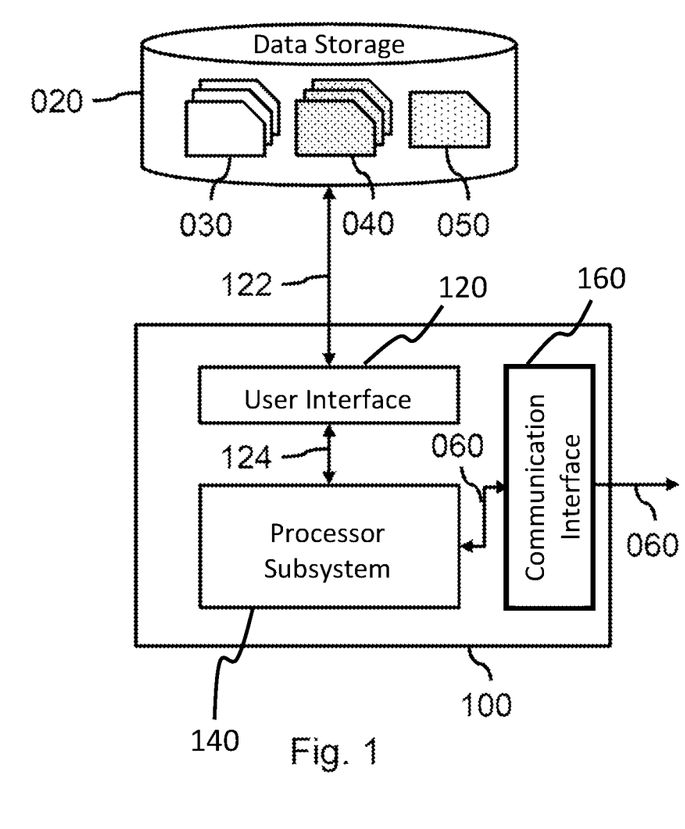
FIG. 1 shows a system for collection of medical image data for machine learning of a machine learnable model, with the system being configured to perform a selection of the medical image data which is in compliance with a privacy policy, which privacy policy limits the selection to a subset of the medical image data.

FIG. 1 shows a system 100 for data collection for machine learning of a machine learnable model. The system 100 may comprise an input interface 120 and a processor subsystem 140 which may internally communicate via data communication 124. The processor subsystem 140 may be configured to, during operation of the system 100 and using the input interface 120, access medical image data 030 of at least one patient and label data 040 defining labels associated with the medical image data, as well as privacy policy data 050 defining one or more computer-readable criteria for limiting a selection of the medical image data to a subset of the medical image data to obfuscate an identity of the at least one patient.

For example, as also shown in FIG. 1, the input interface 120 may provide data access 122 to an external data storage 020 which may comprise said data 030-050. Alternatively, the data 030-050 may be accessed from an internal data storage which is part of the system 100. Alternatively, the data 030-050 may be received via a network from another entity. In general, the input interface 120 may take various forms, such as a network interface to a local or wide area network, e.g., the Internet, a storage interface to an internal or external data storage, etc. The data storage 020 may take any known and suitable form. In some embodiments, the medical image data 030 and the label data 040 may each be accessed from a different data storage than the data storage storing the privacy policy data 050.

The processor subsystem 140 may be further configured to, during operation of the system 100 and based on the one or more computer-readable criteria, perform a selection of the medical image data and an associated selection of the label data to obtain privacy policy-compliant training data 060, and via a communication interface, transmit the privacy policy-compliant training data 060 to another entity associated with the machine learning of the machine learnable model. As also shown in FIG. 1, the communication interface 160 may be an external communication interface such as a network interface to a local or wide area network, e.g., the Internet, via which the other entity may be reachable.

Alternatively, as also discussed with reference to FIG. 5, the communication interface may be an internal interface, e.g., to a further internal processor subsystem (not shown in FIG. 1).

Various details and aspects of the operation of the system 100, including optional aspects, will be further elucidated elsewhere in this specification.

In general, the system 100 may be embodied as, or in, a single device or apparatus, such as a workstation, e.g., laptop or desktop-based, or a server. The device or apparatus may comprise one or more microprocessors which execute appropriate software. For example, the processor subsystem may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the functional units of the system, e.g., the input interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses, such as distributed servers, e.g., in the form of cloud computing.

Figure 2:
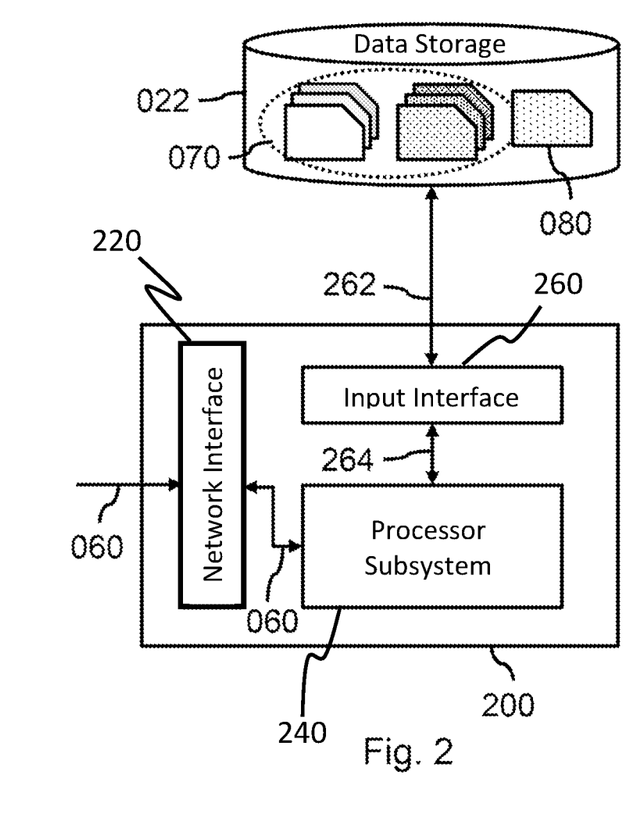
FIG. 2 shows a system for training a machine learnable model based on training data, with the system being configured to request a data collection system to transmit training data associated with a selection of medical image data.

FIG. 2 shows a system 200 for training a machine learnable model using training data obtained from at least one other system. For that purpose, the system 200 may comprise a network interface 220 to a local or wide area network, e.g., the Internet, and an input interface 260 for accessing a data storage, such as an external data storage 022, via external 262 and internal 264 data communication. The data storage 022 may comprise model data 080 defining the machine learnable model. The data storage 022 may also be used by the system 200 to store and access the training data received from different systems, which is shown in FIG. 2 as aggregated training data 070. It will be appreciated that the input interface 260 and the data storage 022 may take similar forms as the input interface 120 and the data storage 020 as described with reference to FIG. 1. The system 200 may further comprise a processor subsystem 240 which may be configured to, during operation of the system 200 and using the network interface 220, request the at least one other system to transmit training data associated with a selection of medical image data, and in response to said request, receive the training data 060 from the at least one other system, and train the machine learnable model based on the training data 060. In some embodiments, the training of the machine learnable model may be based on aggregated training data 070 received from different systems.

In general, the system 200 may be embodied as, or in, a single device or apparatus, such as a workstation, e.g., laptop or desktop-based, or a mobile device. The device or apparatus may comprise one or more microprocessors which execute appropriate software. For example, the processor subsystem may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the functional units of the system, e.g., the input interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 200 may also be implemented in a distributed manner, e.g., involving different devices or apparatuses, such as distributed servers, e.g., in the form of cloud computing.

Figure 3:
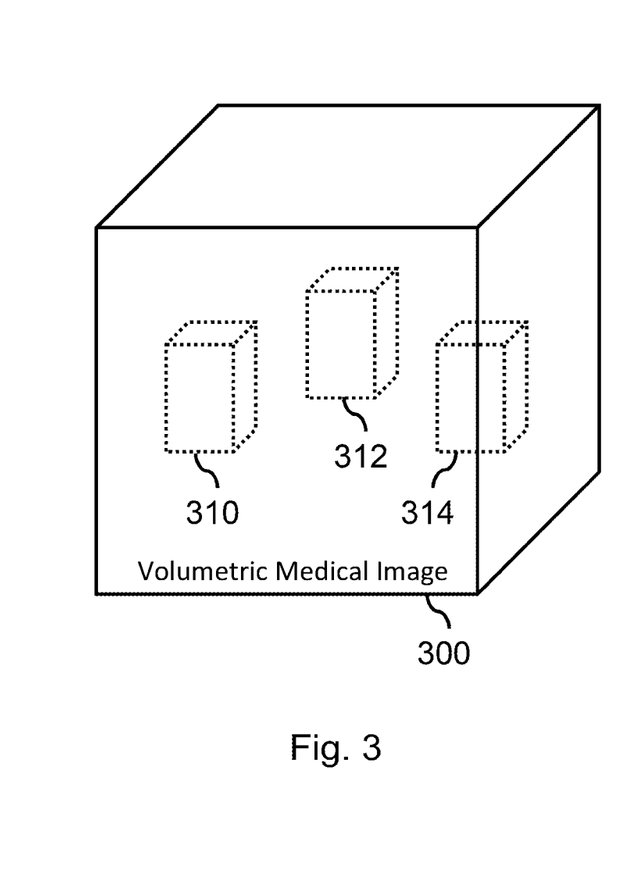
FIG. 3 illustrates the privacy policy limiting the selection of image data of a volumetric image to a number of spatially distributed sub-volumes.

FIG. 3 relates to the selection of the medical image data by the data collection system and method, and illustrates a privacy policy limiting the selection of medical image data to a subset of the medical image data. In this example, the medical image data is volumetric medical image data 300 (also simply referred to as 'volumetric image data') and the privacy policy may limit the selection to a number of sub-volumes 310-314 of the volumetric image data. In a more basic example, the computer-readable criteria may limit the number of sub-volumes, e.g., to three, per volumetric image or per patient, while additionally defining a maximum individual and/or aggregated size of the sub-volumes. The size may for example be defined in relation to the image volume, e.g., as a percentage. In a more complex example, the computer-readable criteria may additionally or alternatively define a spatial, temporal or spatiotemporal distribution of the sub-volumes, e.g., to establish a minimum distance between the sub-volumes and/or a spatial and/or temporal randomness in the selection. In other more complex examples, the computer-readable criteria may, in limiting the selection, take into account which medical image data was previously sent to the same entity (e.g., a training system). For example, the computer-readable criteria may define limitations which also take into account the number, size, distribution, etc., of previously sent selections of the medical image data.

Figure 4:
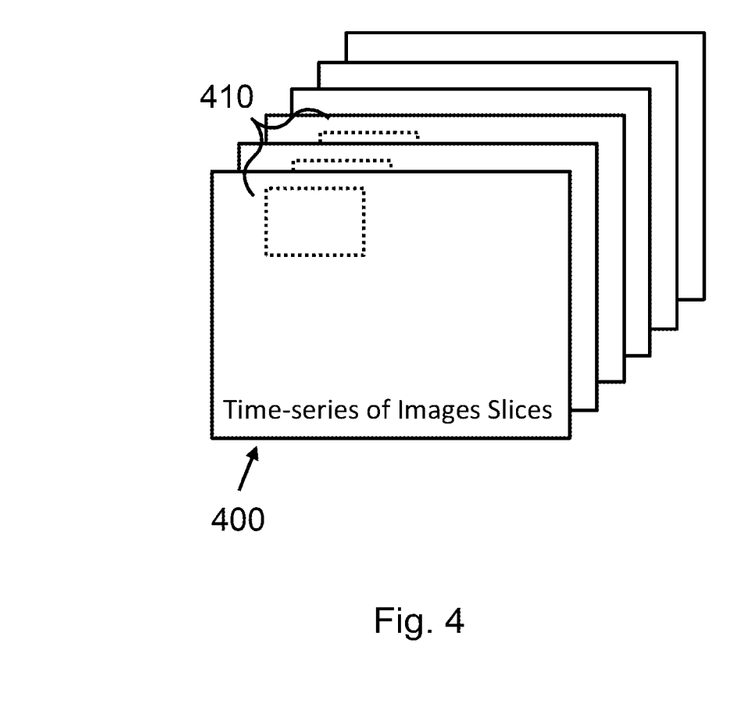
FIG. 4 illustrates the privacy policy limiting the selection of a time-series of image slices to an image region across multiple image slices.

FIG. 4 shows a time-series of image slices 400, and illustrates a privacy policy limiting the selection of the time-series of image slices to an image region 410 across multiple image slices, which may therefore represent a spatiotemporal image region. Similar to the FIG. 3 example, also in this example the privacy policy may limit the selection of the spatiotemporal image region to an image region having a maximum size, e.g., spatially and/or temporally. A maximum spatial size may for example be defined in relation to the image slice's dimensions, e.g., as a percentage, such as 5%, 10% or 20%. A maximum temporal size may for example be defined as a maximum number of image slices, e.g., 1 or 3 or 5, or as a percentage. FIG. 4 by shows a selection 410 across three image slices.

In addition to limiting the selection of medical image data, the privacy policy-compliant training data may also be generated to hide whether image regions belong to a same patient or whether an image region is from an original image or resulting from data augmentation. This may, for example, be achieved by randomly mixing indices corresponding to patient number, original or augmented image region.

Figure 5:
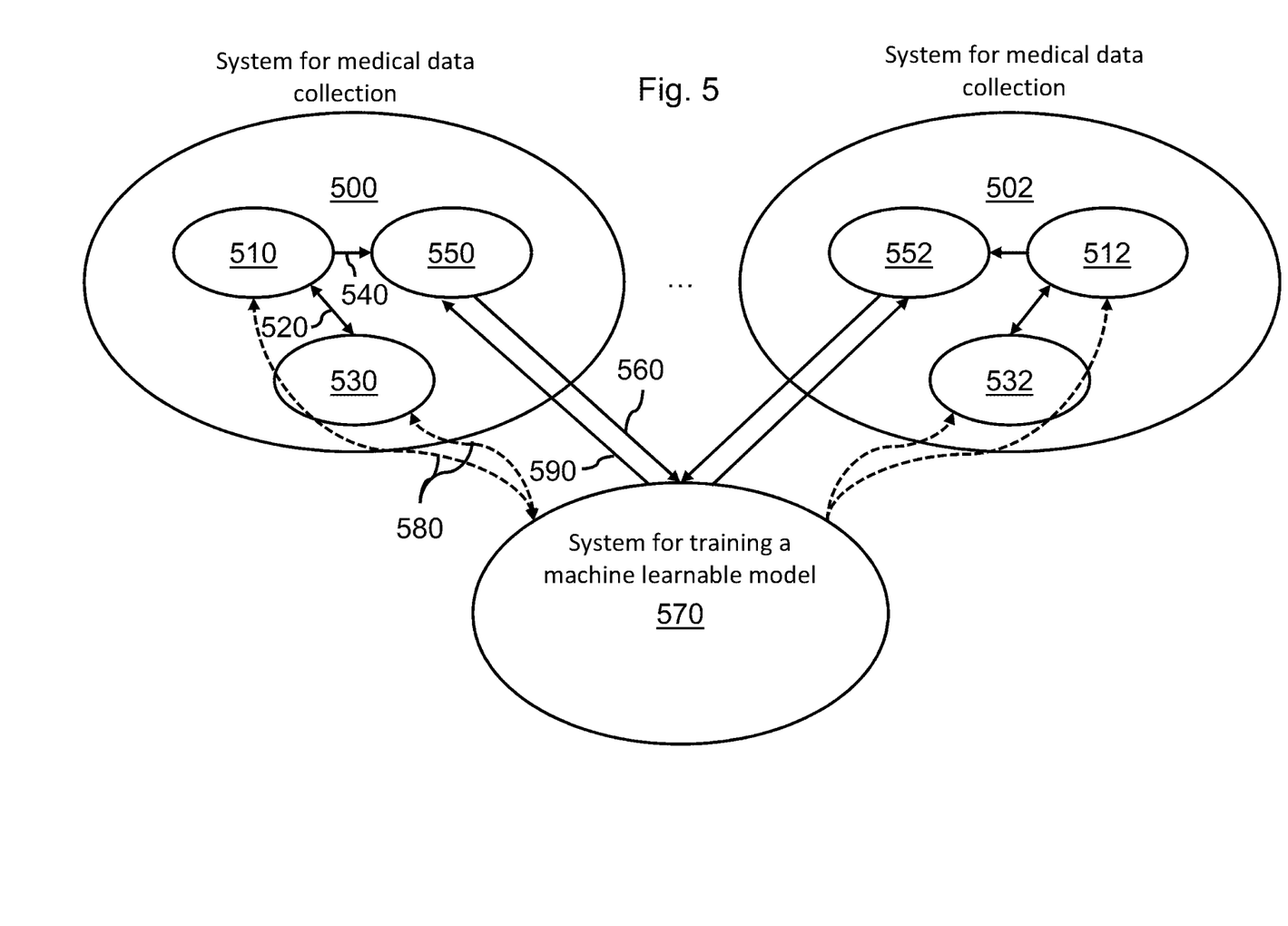
FIG. 5 illustrates different data collection systems at different clinical sites each transmitting training data to a training system, in which the training data comprises a processing result which is obtained by the respective data collection system by processing a privacy policy-compliant selection of medical image data.

FIG. 5 illustrates a particular embodiment of the measures described in this specification, in which different data collection systems 500, 502, which may be located at different clinical sites, each transmit training data to a training system 570, and in which the training data comprises a processing result which is obtained by the respective data collection system by processing a privacy policy-compliant selection of medical image data. Accordingly, FIG. 5 relates to the privacy policy-compliant training data not being sent directly to the training system 570 but rather to a further processor subsystem of each data collection system 500, 502, which processes the privacy policy-compliant training data using a processing algorithm, and which then transmits the processing result as training data to the training system 570.

In this particular example, the processor subsystem described with FIG. 1 and others may be partitioned over a data collection subsystem 510, 512 and a privacy policy subsystem 530, 532, whereas the further processor subsystem is embodied by an evaluation subsystem 550, 552. Here, the term 'evaluation' refers to the processing being in some embodiments an evaluation, with the term 'evaluation' referring to the step of machine learning which precedes the optimization step, e.g., implementing an evaluation function (also referred to as utility function, loss function, scoring function, or fitness function). Effectively, the machine learning may in this embodiment be distributed over the evaluation subsystem 550, 552 performing the evaluation step of the machine learning, and the training system 570 performing the subsequent optimization step based on the evaluation results which are obtained in the form of training data from one or more data collection subsystems 510, 512. Accordingly, FIG. 5 effectively shows a distributed machine learning architecture which may inherently respect privacy regulations and legal requirements.

In a more specific example following the FIG. 5 example, the data collection subsystem 510, 512 may receive a request 580 for training data from the training system 570. In response to the request 580, the data collection subsystem 510, 512 may internally perform a selection 540 of medical image data and labels from a database (e.g. PACS, HIS, clinical workstation, . . . ) which complies with the privacy policy and transmit the selection 540 to the evaluation subsystem 550, 552. To ensure compliance with the privacy policy, the data collection subsystem 510, 512 may communicate via internal data communication 520 with the privacy policy subsystem 530, 532. For example, the data collection subsystem 510, 512 may verify with the privacy policy subsystem 530, 532 whether the request 580 is in compliance with the privacy policy. Such verification by the data collection subsystem 510, 512 may take place before or after selection of the medical image data. For example, the privacy policy subsystem 530, 532 may confirm the request as being in compliance with the privacy policy or not, and if the request is not in compliance, perform or indicate modifications to the request whereby compliance with the privacy policy is established. In other embodiments, the privacy policy subsystem 530, 532 may receive the request 580 from the training system 570 and determine whether the request is in compliance with the privacy policy. The privacy policy subsystem 530, 532 may confirm the compliance by forwarding the request 580 to the data collection subsystem 510, 512 via internal data communication 520, or if the request 580 is not in compliance with the privacy policy, modify the request 580 to obtain a modified request which is in compliance with the privacy policy and transmit the modified request to the data collection subsystem 510, 512.

The architecture shown in FIG. 5 may be advantageously used as follows. An R&D user may define a training task in combination with a request for training data for the training system 570. The training system 570, which may be considered to function a training coordinator, may send the request as request data 580 to the data collection system 500, 502, which may be embodied by an IT system in the hospital that collects medical image data sets in combination with labels from other systems (e.g. PACS or HIS system, clinical workstations, . . . ) and which makes the medical image data and labels available for training. In particular, the training system 570 may coordinate evaluations of the training data required for machine learning. The machine learning may involve training a machine learnable model, which may involve applying a machine learning algorithm A(w, I, p) to an image I (e.g. an MR, CT or US image, an image sequence, or a multi-modal PET-CT image) as a function of further parameters p characterizing for example patient information (age, sex, patient history, previous diseases, . . . ) and as a function of a possibly large number of parameters w. For a specific restricted implementation, it is assumed that the algorithm can be applied to (small) sub-images $I_s$.

For example, the machine learning algorithm A(w, I, p) may be represented a neural network with parameters w that classifies the image into different types of images or disease classes (e.g., ResNet). The neural network may for example be a Convolutional Neural Network (CNN) for image segmentation and may be applied to image regions, such as sub-volumes of volumetric images. Another example is a neural network for boundary detection in model-based segmentation. The machine learning may involve optimizing the parameters w of the algorithm by minimizing or maximizing a metric M that compares the algorithm result A(w, $I_i$, $p_i$) (e.g., a segmentation of an organ in the image or the classification into a disease class) with reference labels $R_i$ over a database with N samples:

$$w_{learned} = \mathrm{argmin}_w M(R_1, A(w, I_1, p_1), \ldots, R_N, A(w, I_N, p_N))$$

In some embodiments, the training system 570 may coordinate the optimization by sending requests 580 to respective data collection systems 500, 502, by receiving evaluation results 560 from their respective evaluation subsystems 550, 552 and by performing machine learning using the evaluation results 560. The resulting machine learned model may then be made available to a R&D user.

In some embodiments, the evaluation algorithm to be applied by the evaluation subsystem 550, 552 may be defined by R&D users and transferred, for example, in a data container 590, to the evaluation subsystem 550, 552. If training can be performed on small image regions (e.g. when using convolutional neural networks or training boundary detectors for model-based segmentation), the evaluation subsystem 550, 552 may directly transfer image regions together with the corresponding labels to the training system 570. Otherwise, the evaluation subsystem 550, 552 may evaluate the medical image data and labels using the transferred evaluation algorithm. The training system 570 may then collect the evaluation results sent by the evaluation subsystem 550, 552 and use the evaluation results to complete evaluation and optimization of the algorithm A(w, $I_i$, $p_i$).

Figure 6:
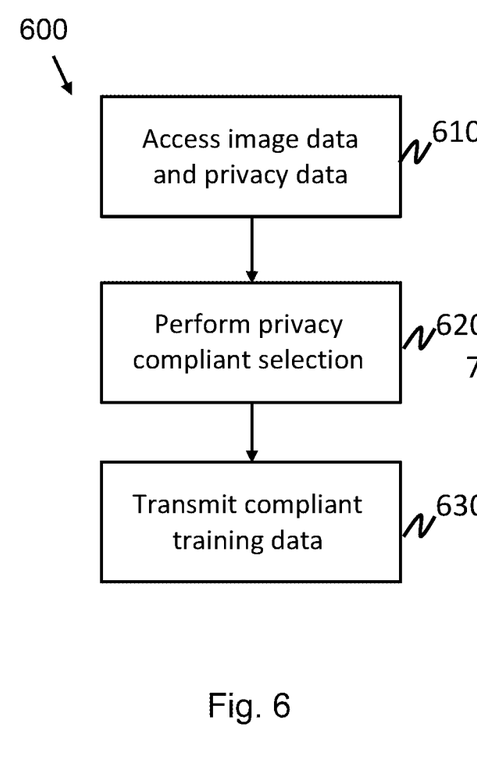
FIG. 6 shows a method for medical data collection.

FIG. 6 shows a block-diagram of computer-implemented method 600 for data collection for distributed machine learning of a machine learnable model. The method 600 may correspond to an operation of the system 100 of FIG. 1. However, this is not a limitation, in that the method 600 may also be performed using another system, apparatus or device.

The method 600 may comprise, in an operation titled "ACCESSING LABELLED IMAGE DATA, PRIVACY POLICY DATA", accessing 610 medical image data of at least one patient and label data defining labels associated with the medical image data, and privacy policy data defining one or more computer-readable criteria for limiting a selection of the medical image data to a subset of the medical image data to obfuscate an identity of the at least one patient. The method 600 may further comprise, in an operation titled "PERFORMING PRIVACY POLICY-COMPLIANT SELECTION", based on the one or more computer-readable criteria, performing 620 the selection of the medical image data and an associated selection of the label data to obtain privacy policy-compliant training data.

The method 600 may further comprise, in an operation titled "TRANSMITTING PRIVACY POLICY-COMPLIANT TRAINING DATA", via a communication interface, transmitting 630 the privacy policy-compliant training data to another entity to enable the machine learnable model to be trained on the basis of the privacy policy-compliant training data.

Figure 7:
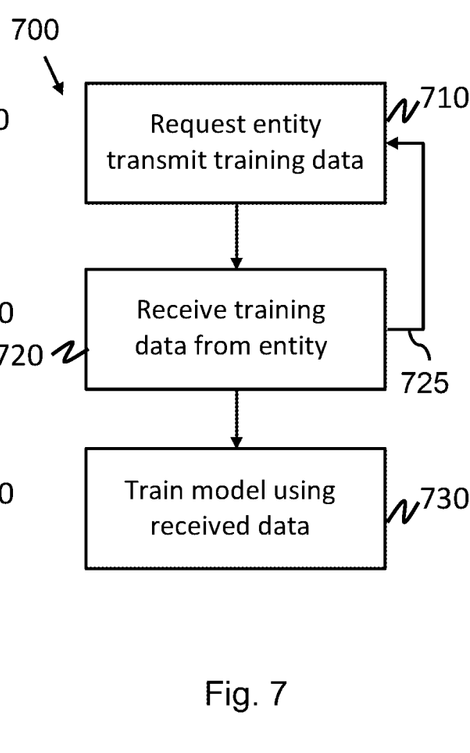
FIG. 7 shows a method for training a machine learnable model.

FIG. 7 shows a block-diagram of computer-implemented method 700 for training a machine learnable model using training data obtained from a number of entities which are reachable via a network. The method 700 may correspond to an operation of the system 200 of FIG. 2. However, this is not a limitation, in that the method 700 may also be performed using another system, apparatus or device.

The method 700 may comprise, in an operation titled "REQUESTING ENTITY TO TRANSMIT TRAINING DATA", via a network, requesting 710 at least one of the entities to transmit training data associated with a selection of medical image data. The method 700 may further comprise, in an operation titled "RECEIVING TRAINING DATA FROM ENTITY", via the network and in response to said request, receiving 720 the training data from the at least one entity. The method 700 may further comprise, in what may be an optional operation titled "REPEATING STEPS FOR ANOTHER ENTITY", repeating 725 the aforementioned steps 710, 720 in respect of at least one other entity. The method 700 may further comprise, in an operation titled "TRAINING MODEL BASED ON RECEIVED TRAINING DATA", training 730 the machine learnable model based on the training data.

It will be appreciated that, in general, the operations of method 600 of FIG. 6 and/or method 700 of FIG. 7 may be performed in any suitable order, e.g., consecutively, simultaneously, or a combination thereof, subject to, where applicable, a particular order being necessitated, e.g., by input/output relations.

Figure 8:
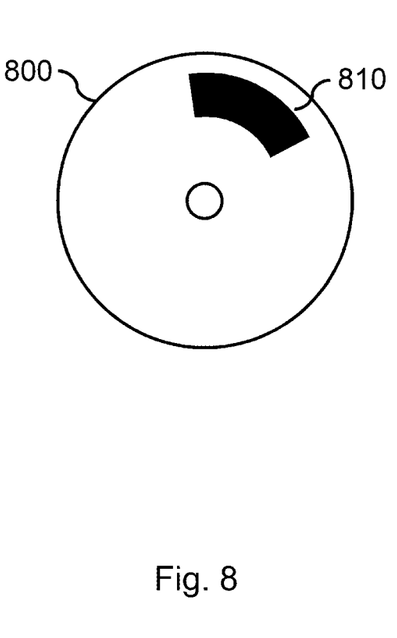
FIG. 8 shows a computer-readable medium comprising data.

The method(s) may be implemented on a computer as a computer implemented method, as dedicated hardware, or as a combination of both. As also illustrated in FIG. 8, instructions for the computer, e.g., executable code, may be stored on a computer readable medium 800, e.g., in the form of a series 810 of machine-readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 8 shows an optical disc 800. Alternatively, the computer readable medium 800 may comprise transitory or non-transitory data 810 representing the privacy policy data as described elsewhere in this specification.

Examples, embodiments or optional features, whether indicated as non-limiting or not, are not to be understood as limiting the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for data collection for machine learning of a machine learnable model, the system comprising:
   one or more hardware processors;
   a communication interface to another entity associated with training of a machine learnable model; and
   a memory storing instructions to:
   receive a request for training data from the other entity;
   access:
      medical image data of at least one patient and label data defining labels associated with the medical image data; and
      privacy policy data defining one or more computer-readable criteria for limiting a selection of the medical image data to a subset of the medical image data to obfuscate an identity of the at least one patient;
   verify whether the request is in compliance with the privacy policy data;
   based on the one or more computer-readable criteria, automatically perform, by the one or more hardware processors, the selection of the medical image data and an associated selection of the label data to obtain privacy policy-compliant training data, wherein the selection is limited to one or more image regions of the medical image data; and
   via the communication interface, transmit the privacy policy-compliant training data to the other entity to enable the machine learnable model to be trained on the basis of the privacy policy-compliant training data.

2. The system according to claim 1, wherein the one or more computer-readable criteria limit at least one of the group of:
   a number,
   an individual or aggregate size, and
   a distribution,
   of the one or more image regions per image or per patient.

3. The system according to claim 1, wherein the memory stores further instructions to apply a machine learning data augmentation technique to the medical image data before selecting and transmitting the privacy policy-compliant training data to the other entity.

4. The system according to claim 1, wherein the memory stores further instructions to, before or when generating the privacy policy-compliant training data, obfuscate one or more of whether:
   different subsets of the medical data, or different parts of a subset, belong to a same patient; or
   the subset of the medical image data, or a part of the subset, is augmented by a machine learning data augmentation technique.

5. The system according to claim 4, wherein the memory stores further instructions to randomize or pseudo-randomize an identifier of each of the different subsets of the medical image data, and/or an identifier of each of the different parts of the subset.

6. The system according to claim 1, wherein the memory stores further instructions to determine whether the request, individually and/or in aggregate with previous requests, exceeds said limitation defined by the one or more computer-readable criteria, and when the limitation is exceeded, reject the request.

7. The system according to claim 1, wherein the memory stores further instructions to:
- via the network interface, receive a processing algorithm for processing the selection of the medical image data;
- execute the processing algorithm to obtain a processing result; and
- via the network interface, transmit the processing result as training data to a training system which is configured to train the machine learnable model based on the processing result provided by the training data.

8. A computer-implemented method for data collection for distributed machine learning of a machine learnable model, the method comprising:
- receiving, by a system comprising one or more processors, a request for training data;
- accessing:
  - medical image data of at least one patient and label data defining labels associated with the medical image data;
  - privacy policy data defining one or more computer-readable criteria for limiting a selection of the medical image data to a subset of the medical image data to obfuscate an identity of the at least one patient;
- verifying whether the request is in compliance with the privacy policy data;
- based on the one or more computer-readable criteria, automatically performing, by the one or more processors, the selection of the medical image data and an associated selection of the label data to obtain privacy policy-compliant training data, wherein the selection is limited to one or more image regions of the medical image data; and
- via a communication interface, transmitting the privacy policy-compliant training data to another entity to enable the machine learnable model to be trained on the basis of the privacy policy-compliant training data.

9. A non-transitory computer-readable storage medium comprising instructions arranged to cause one or more processors to:
- receive a request for training data;
- access medical image data of at least one patient and label data defining labels associated with the medical image data;
- access privacy policy data defining one or more computer-readable criteria for limiting a selection of the medical image data to a subset of the medical image data to obfuscate an identity of the at least one patient;
- verify whether the request is in compliance with the privacy policy data;
- based on the one or more computer-readable criteria, automatically perform the selection of the medical image data and an associated selection of the label data to obtain privacy policy-compliant training data, wherein the selection is limited to one or more image regions of the medical image data; and
- via a communication interface, transmit the privacy policy-compliant training data to another entity to enable the machine learnable model to be trained on the basis of the privacy policy-compliant training data.

* * * * *